(12) United States Patent
Lenna et al.

(10) Patent No.: US 8,119,793 B2
(45) Date of Patent: Feb. 21, 2012

(54) PROCESS FOR PREPARING BUDESONIDE

(75) Inventors: Roberto Lenna, San Giorgio Su Legnano (IT); Maurizio Montoro, Origgio (IT)

(73) Assignee: Industriale Chimica S.r.L., Milan (IT)

( * ) Notice: Subject to any disclaimer, the term of this patent is extended or adjusted under 35 U.S.C. 154(b) by 459 days.

(21) Appl. No.: 12/418,893

(22) Filed: Apr. 6, 2009

(65) Prior Publication Data

US 2009/0259037 A1 Oct. 15, 2009

(30) Foreign Application Priority Data

Apr. 11, 2008 (IT) .............................. MI2008A0645

(51) Int. Cl.
*C07J 71/00* (2006.01)
(52) U.S. Cl. ........................................................ 540/63
(58) Field of Classification Search ...................... 540/63
See application file for complete search history.

(56) References Cited

U.S. PATENT DOCUMENTS 5,733,901 A    3/1998  Gutterer

FOREIGN PATENT DOCUMENTS

| DE | 270 917 A5 | 8/1989 |
| EP | 0 164 636 A | 12/1985 |
| EP | 0 875 516 A2 | 11/1998 |
| GB | 1 429 922 A | 3/1976 |
| GB | 1 469 575 | 4/1977 |
| WO | WO 92/11280 | 7/1992 |

OTHER PUBLICATIONS

Thomson Scientific ~ Database WPI; "Preparing Budesonide . . . "; Oct. 8, 2008; 4 pgs.
Michael Aston et al.,; "Anti-Inflammatory . . . "; American Chemical Society; 1996; pp. 4888-4896.
European Pharmacopoeia; "Budesonide", p. 1342, 2008.

*Primary Examiner* — Brenda Coleman
(74) *Attorney, Agent, or Firm* — Stetina Brunda Garred & Brucker

(57) ABSTRACT

A process is described for preparing budesonide which comprises the steps of: a) preparing an aqueous hydrochloric acid solution; b) reacting 16α-hydroxyprednisolone and butyraldehyde within the solution prepared in step a), in an inert atmosphere; c) quenching the reaction of step b) with water. The process of the invention enables the ratio between the A and B epimers of budesonide to be controlled.

17 Claims, No Drawings

PROCESS FOR PREPARING BUDESONIDE

CROSS-REFERENCE TO RELATED APPLICATIONS

Not Applicable

STATEMENT RE: FEDERALLY SPONSORED RESEARCH/DEVELOPMENT

Not Applicable

FIELD OF THE INVENTION

The present invention concerns a process for preparing (11β,16α)-16,17-[butylidenebis(oxy)]-11,21-dihydroxypregna-1,4-diene-3,20-dione of formula (I)

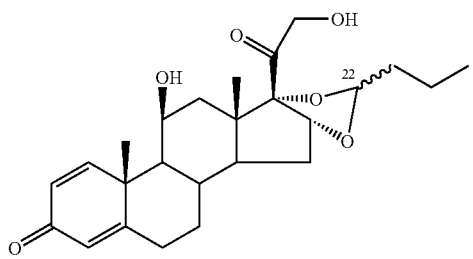

also known by the name of budesonide.

BACKGROUND

Budesonide is a synthetic steroid with anti-inflammatory activity, used for preparing pharmaceutical compositions for the treatment of chronic and acute asthma of particular severity.

Budesonide and other structurally similar glucocorticoids were described for the first time in patent GB 1,429,922 in the name of the Bofors company.

Specifically, the budesonide compound was prepared in example 9 by reaction between 11β,16α,17α,21-tetrahydroxypregna-1,4-diene-3,20-dione, i.e. 16α-hydroxyprednisolone, and butyraldehyde in dioxane as solvent and perchloric acid as catalyst. At page 2, line 8 onwards, p-toluenesulphonic acid and hydrochloric acid as acid catalysts are also proposed, and a solvent equivalent to dioxane as the solvent. The solution, treated with methylene chloride, was then neutralized and the acetal formed was isolated by column chromatography purification on gel. According to the document, the final product is a mixture of stereoisomers which can be separated by gel filtration, for example as described in GB 1,428,416.

The budesonide compound is actually a mixture of two epimers, different for the spatial arrangement of the substituents at the carbon 22 atom of the dioxolane ring of the compound of formula (I). Specifically, the isomer with S configuration is commonly defined as epimer A, and the isomer with R configuration as epimer B (European Pharmacopeia 6.0, Budesonide, page 1342).

The currently employed synthesis for budesonide production, which enables an A/B epimer ratio of about 1/1 to be obtained, is still based on the reaction of 16α-hydroxyprednisolone (11β,16α,17α,21-tetrahydroxypregna-1,4-diene-3,20-dione) with butyraldehyde in dioxane, using perchloric acid as catalyst.

Although from the pharmacological viewpoint the R-epimer is the most active one, from the practical viewpoint, commercial authorization for budesonide can however only be obtained for specific epimeric ratios of R and S stereoisomers.

Document EP 875,516 in the name of Pharmabios then proposed a budesonide synthesis, enabling epimer distribution at position C-22 to be controlled, by reaction between 16α-hydroxyprednisolone and butyraldehyde in the presence of an aqueous hydrohalic acid chosen from hydrobromic acid and hydriodic acid, in which the hydrohalic acid is used both as solvent and catalyst. In the document, the use of hydrobromic acid (HBr) in aqueous solution is described as particularly advantageous, and considered as feature distinguishing from hydrochloric acid, due to the high solvent power of aqueous HBr which allows the acetylization to be conducted in the homogeneous phase thus controlling in a reliable way the ratio between the epimers.

Controlling the ratio between epimers A and B is therefore a problem related to the marketing of budesonide. Specifically, according to the European Pharmacopeia, the budesonide product must contain an epimer A percentage of between 40 and 51%, the remainder being epimer B; and, according to the US Pharmacopeia, the quantity of epimer A must be comprised between 44 and 51%. This percentage of epimer A is present in the crude reaction product of the methods currently used for budesonide production. Said methods however comprise a step of crystallization from methanol which, during the crystallizations, progressively reduces the quantity of epimer A as it is more soluble in methanol than epimer B.

This solubility difference between epimers A and B limits the number of crystallizations applicable to the crude product. There is therefore the problem of striking a balance between the desired purity requirement of the final product and the minimum quantity of epimer A demanded in the diastereoisomer mixture constituting budesonide.

An object of the present invention is therefore to obtain a quantity of epimer A directly from the condensation reaction such that even with the crystallizations needed to purify the product, an epimer A percentage quantity within the range from 44% to 51% is always achieved.

A further object of the invention is therefore to provide a final budesonide product that satisfies the requirements of both the EU Pharmacopeia and the US Pharmacopeia.

BRIEF SUMMARY

The aforesaid object has been achieved by means of a process for preparing budesonide of formula (I),

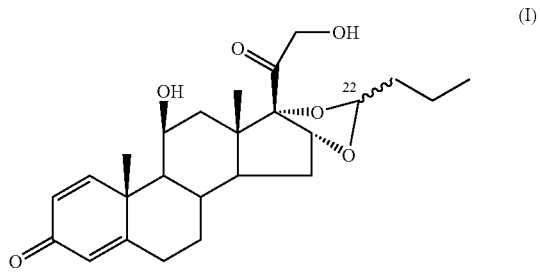

which comprises the steps of:
a) preparing an aqueous hydrochloric acid solution;
b) reacting 16α-hydroxyprednisolone and butyraldehyde within the solution prepared in step a) in an inert atmosphere;

c) quenching the reaction of step b) with water or an aqueous solution.

The process of the invention enables the epimer distribution at position 22 of the final product to be controlled, according to the reaction conditions, such that in both the crude reaction product and the final product the epimer A quantity is from 44 to 51%.

The characteristics and advantages of the invention will become evident from the detailed description that follows.

DETAILED DESCRIPTION

The invention therefore concerns a process for the preparation of budesonide of formula (I) which comprises the steps of:

a) preparing an aqueous hydrochloric acid solution; b) reacting 16α-hydroxyprednisolone and butyraldehyde within the solution prepared in step a) in an inert atmosphere; and c) quenching the reaction of step b) with water or an aqueous solution.

In step a) a hydrochloric acid solution is prepared.

Preferably the hydrochloric acid can be prepared by diluting concentrated hydrochloric acid with water in a ratio of concentrated hydrochloric acid to water within the range from 6/4 to 9/1. More preferably, the concentrated hydrochloric acid/water ratio is about 7/3, and even more preferably said ratio is about 8/2, i.e. 8 parts of concentrated hydrochloric acid to 2 of water.

Advantageously, the aqueous hydrochloric acid solution is a solution obtainable from finning or concentrated commercial hydrochloric acid at 36-37% and water. To prepare the aqueous hydrochloric acid solution in the preferred ratios, the use of hydrochloric acid in the gaseous phase is not necessary. It is therefore unnecessary to provide a plant dedicated to the handling of a corrosive gas.

The reaction between 16α-hydroxyprednisolone and butyraldehyde of step b) can be represented as follows:

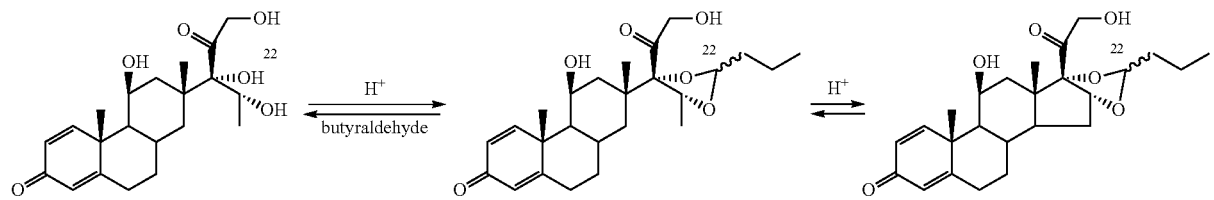

The reactant of step b) of the present process, i.e. 16α-hydroxyprednisolone (11β,16α,17α,21-tetrahydroxypregna-1,4-diene-3,20-dione) is a known commercial product available on the market.

Preferably, the reaction temperature of step b) varies within the range from −5 to +15° C., more preferably from 0 to +5° C. and the reaction time of step b) varies within the range from 60 to 240 minutes, and even more preferably from 120 to 180 minutes.

Advantageously in step b) the butyraldehyde reactant is used in slight excess over 16α-hydroxyprednisolone.

In step c), takes place the quenching of the reaction of step b) with water or an aqueous solution. Preferred for carrying out this step is the use of water or of an aqueous solution being a buffer system, or capable of forming a buffer system upon mixture with the product of step b), such as a sodium acetate aqueous solution; in the following, for the quenching step reference will be made to the use of water, but is intended that aqueous solutions can be used as well. Preferably, said step is carried out by pouring water pre-cooled to T<10° C. into the reaction container or, by pouring the mixture in the reaction container of step b) into water pre-cooled to T<10° C. More preferably, the reaction mixture is poured into water pre-cooled to T<5° C., using a volume of quenching water at least twice the volume of aqueous acidic reaction solution.

In the preferred embodiment, the process of the invention also comprises the steps of:

d) recovering the crude budesonide reaction compound from the reaction mixture of step c);

e) neutralizing and dehydrating;

f) crystallizing from isopropyl ether to obtain crystallized crude budesonide;

g) crystallizing the crystallized crude budesonide compound with methanol to obtain pure budesonide.

Preferably, step d) of recovering the reaction compound of step c) takes place by extraction with a solvent or by filtration. The extraction solvent can be a common organic solvent non-water miscible and inert in an acid environment; preferably methylene chloride is used in step d).

The neutralization in step e) can be carried out with basic washes (for example with a potable water-sodium bicarbonate solution) or neutral washes (for example with potable water) applied to the solution, preferably methylenic, of the budesonide from the reaction.

Dehydrating the neutralized product of step e) can advantageously be achieved by adding anhydrous sodium sulphate.

The crystallization step f) is conducted in isopropyl ether. Preferably the crystallization step consists of adding the isopropyl ether to the neutralized and dried methylenic solution followed by distillation. The distillation is preferably conducted at atmospheric pressure at a temperature of 60-65° C.

The budesonide compound obtained at the end of step f) by the aforedescribed process exhibits an excellent degree of purity which is nevertheless further increased by subjecting the product to a purification step by crystallization from methanol.

Preferably the step g) of crystallization with methanol consists of the following substeps:

1) boiling the crude budesonide of step f) in a volume of methanol such as to achieve total dissolution;

2) distilling off the methanol, preferably at atmospheric pressure;

3) cooling the obtained suspension.

Advantageously, the residual volume (measured in liters) of methanol at the end of distillation is twice the 16α-hydroxyprednisolone weight (measured in kilograms) used in the reaction. Preferably the suspension is cooled for a time between 1 and 2 hours.

The crystallized budesonide is then dried under reduced pressure.

Preferably, the drying is conducted at a temperature between 35 and 55° C. for a time ranging from 2 to 48 hours, more preferably at a temperature between 40 and 50° C. for a time ranging from 12 to 24 hours.

Where possible the aforesaid substeps 1)-3) are advantageously conducted in an inert atmosphere using nitrogen.

By the process of the invention a crude budesonide compound, in high yields and with a high degree of purity exceeding 90%, is already obtained at the crude reaction product stage leaving step f).

The process of the invention therefore achieves its purpose without requiring a costly and industrially inconvenient redefinition of the crude product purification process and, even more advantageously, by using only hydrochloric acid in solution as both the reaction catalyst in step b) and the solvent, thus avoiding the use of polluting organic solvents.

Advantageously, the process of the invention also allows budesonide to be obtained in high yields and with a high degree of purity already as a crude reaction product before final purification and in the required epimer percentages both after step f) and at the end of the process after final purification.

In contrast to what is stated in document EP 875,516, which proposes hydrobromic acid or hydriodic acid, the inventors of the present invention have provided a mixture of budesonide epimers which satisfies current needs by means of a process that uses only a hydrochloric acid solution. Moreover, hydrochloric acid in comparison with hydrobromic acid and hydriodic acid is definitely more manageable, less costly and is easily available for industrial use.

EXAMPLES

Some examples of the process of the invention are given below by way of non limiting illustration.

Example 1

An HCl solution was prepared using 8 volumes of concentrated technical HCl at 36.5% and 2 volumes of water.

240 ml of the hydrochloric acid solution were fed into a flask, and the solution cooled to 0° C./+5° C. 30.0 g of 16α-hydroxyprednisolone were added in portions and the solution agitated at this temperature for about 5 minutes until complete dissolution.

While maintaining the solution at 0<T<+5° C., 12.0 ml of butyraldehyde were added over a period of 5 minutes.

The reaction was almost instantaneous and completed in 5 minutes (as confirmed by TLC).

The solution was then maintained at 0° C./+5° C., while monitoring the ratio between epimer A and epimer B by HPLC (for a total reaction time of 2 hours, 15 minutes).

A water/sodium acetate solution, previously prepared and cooled to 0° C./+5° C., was then poured in to quench the reaction.

The mixture was then subjected to agitation for 30 minutes, checking that the pH was greater than 4.0. The crude reaction product was then filtered off and washed with water.

The wet product was dissolved with 180 ml of methylene chloride, the water was separated and the methylene phase was washed twice with about 10% of water.

The water was then separated from the methylene phase. 150 ml of diisopropylether were added and the methylene chloride was distilled off at atmospheric pressure, the bath temperature being +65° C.

The crystallized solid was then cooled for 1 hour at 0° C./+5° C.

The crystallized solid was then dried under vacuum at 45° C. for 12 hours.

31 g of crude budesonide were obtained with an epimer A/epimer B ratio equal to 49 A/51 B.

The crude crystallized solid was then subjected to a purification step. Crude budesonide was dissolved in 8 volumes (240 ml; 8 times in liters the starting amount of 16α-hydroxyprednisolone in kg) of methanol and placed under reflux and the mixture treated with decolourizing carbon, filtered and concentrated to 2 volumes by distillation at atmospheric pressure. Once the desired volume was achieved, the solution was cooled to 0° C./+5° C. for 1 hour.

The mass was then filtered, washed with methanol pre-cooled to −10° C. and the solid obtained was dried at 45/50° C. under vacuum for 12 hours. 26.4 g of budesonide were obtained with an epimer A/epimer B ratio equal to 47.9 A/52 B.

Example 2

240 ml of a 8/2 conc. HCl/water solution were fed into a 1 litre flask under a nitrogen stream.

The solution was cooled to 0<T<5° C. and 30 g of 16α-hydroxyprednisolone were added.

The solution was agitated until complete dissolution, in about 20 minutes, after which 12 ml of butyraldehyde were added drop-wise over a 10 minute period, maintaining T<5° C.

HPLC monitoring for the epimer ratio was carried out after 60 minutes and 120 minutes. The results were:

at 60 minutes B=44%, A=55%;
at 120 minutes B=47.3%, A=52%.

The solution was agitated for 2 hours and 30 minutes at T<5° C., after which the reaction solution was poured onto 500 ml of water pre-cooled to T<10° C. The procedure was carried out over a period of about 5 minutes. The suspension was agitated for 40 minutes at T<5° C., and 150 ml of methylene chloride were added, vigorously agitating for 10 minutes before separating the phases.

The aqueous phase was re-extracted with 40 ml of methylene chloride.

The combined organic phases were washed with 150 ml of water, 100 ml of a saturated aqueous sodium bicarbonate solution and 100 ml of water.

The organic phase was taken up with 5 g of sodium sulphate and 0.6 g of carbon. The organic phase was then agitated for 10 minutes before being filtered through celite. The filter cake was washed with methylene chloride.

150 ml of isopropyl ether were added to the methylenic solution, the mixture being distilled at atmospheric pressure and at 65° C. to a residual volume of about 120 ml. The duration of distillation was about 2 hours.

The suspension was cooled and maintained at T<5° C. for 1 hour under agitation. The suspension was filtered, the filtrate was washed with isopropyl ether and air dried to a constant weight, to obtain 31 g of crude budesonide. The epimer A to epimer B ratio in the crystallized crude budesonide was equal to 50.9 A/49.1 B.

The crude budesonide was then refluxed with 310 ml of methanol until complete dissolution.

The solvent was then distilled off at atmospheric pressure to a residual volume of 60-65 ml (about twice in liters the amount of starting 16α-hydroxyprednisolone in kg).

The suspension was cooled and maintained under agitation at T<5° C. for 2 hours. The suspension was then filtered and the filtrate washed with cold methanol.

The washed filtrate was dried for 16 hours at 45° C. under reduced pressure.

27 g of budesonide were obtained which, submitted to complete analysis, satisfied the specifications of the EU and US pharmacopeia.

Epimer A=48.5%.

Example 3

240 ml of a 8/2 conc. HCl/water solution were fed into a 1 litre flask under a nitrogen stream.

The solution was cooled to 0<T<5° C. and 30 g of 16α-hydroxyprednisolone were added.

The solution was agitated until complete dissolution, in about 5 minutes, after which 12 ml of butyraldehyde were added drop-wise over a 10 minute period, maintaining T<5° C.

HPLC monitoring for the epimer ratio was carried out after 60 minutes and 120 minutes.

The ratio between the epimers was:
at 60 minutes B=45.4%, A=54%;
at 120 minutes B=48.1%, A=51.2%.

The reaction solution was agitated for 2 hours and 30 minutes at T<5° C. then poured into 480 ml of water pre-cooled to T<5° C. The procedure was carried out over a period of about 5 minutes.

The suspension was agitated for 30 minutes at T<5° C., then 150 ml of methylene chloride were added, agitating vigorously for 10 minutes before separating the phases.

The aqueous phase was re-extracted with 50 ml of methylene chloride.

The combined organic phases were washed with 50 ml of water, with 65 ml of a saturated aqueous sodium bicarbonate solution and with 50 ml of water.

The organic phase was taken up with 3 g of sodium sulphate and 0.6 g of carbon, then agitated for 25 minutes before being filtered through celite. The filter cake was washed with 30 ml of methylene chloride.

150 ml of isopropyl ether were added to the methylenic solution, the mixture being distilled at atmospheric pressure over a bath at 60-62° C. until distillation was ended. The duration of distillation was about 30 minutes.

The suspension was cooled and maintained under agitation at T<5° C. for 1 hour. The suspension was filtered, the filtrate was washed with 30 ml of isopropyl ether and air dried overnight.

32.5 g of crude budesonide were obtained. The epimer A to epimer B ratio in the crystallized crude budesonide was equal to 50.5 A/49.5 B.

The crude budesonide was then refluxed with 250 ml of methanol until complete dissolution.

The solvent was then distilled off at atmospheric pressure to a residual volume of 60 ml (calculated as the difference between the added and distilled-off solvent; twice in liters the amount of starting 16α-hydroxyprednisolone in kg).

The suspension was cooled and maintained under agitation at T<5° C. for 1 hour. The suspension was filtered and the filtrate washed with cold methanol (2×15 ml).

The washed filtrate was dried for 16 hours at 45° C. under reduced pressure.

27.8 g of budesonide were obtained which, submitted to complete analysis, satisfied the specifications of the EU and US pharmacopeia.

Epimer A=47.4%.

What is claimed is:

1. Process for preparing budesonide of formula (I),

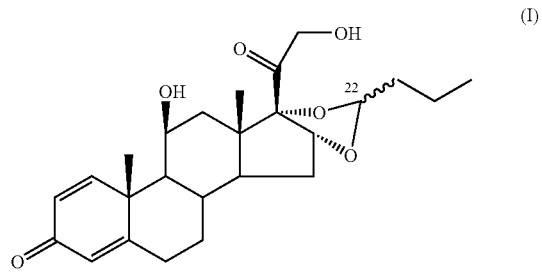

which comprises the steps of:
a) preparing an aqueous hydrochloric acid solution;
b) reacting 16α-hydroxyprednisolone and butyraldehyde within the solution prepared in step a), in an inert atmosphere;
c) quenching the reaction of step b) with water or an aqueous solution.

2. Process according to claim 1, wherein the hydrochloric acid solution in step a) is prepared from concentrated hydrochloric acid and water in a concentrated hydrochloric acid/water ratio within the range, from 6/4 to 9/1.

3. Process according to claim 1, wherein the hydrochloric acid/water ratio is about 7/3.

4. Process according to claim 1, wherein the hydrochloric acid/water ratio is about 8/2.

5. Process according to claim 1, wherein the aqueous hydrochloric acid solution is a solution obtainable from fuming or concentrated commercial hydrochloric acid at 36-37% and water.

6. Process according to claim 1, wherein the reaction temperature of step b) varies within the range from −5 to +15° C.

7. Process according to claim 1, wherein the reaction time of step
b) varies within the range from 60 to 240 minutes.

8. Process according to claim 1, wherein in step b) the butyraldehyde reactant is used in slight excess over 16α-hydroxyprednisolone.

9. Process according to claim 1, wherein in step c) an aqueous solution of sodium acetate is used for quenching the reaction of step b).

10. Process according to claim 1 wherein the process of the invention further comprises the steps of:
d) recovering the crude budesonide reaction compound from the reaction mixture of step c);
e) neutralizing and dehydrating;
f) crystallizing from isopropyl ether to obtain crystallized crude budesonide;
g) crystallizing the crystallized crude budesonide with methanol to obtain pure budesonide.

11. Process according to claim 10, wherein recovery of the reaction compound of step c) takes place by extraction with the solvent methylene chloride.

12. Process according to claim 10, wherein step g) of crystallization with methanol comprises the following sub-steps:
1) boiling crude budesonide from step f) in a volume of methanol to achieve total dissolution;
2) distilling the methanol;
3) cooling the suspension obtained.

13. Process according to claim 10, wherein after step g) of crystallization from methanol budesonide is obtained with 44%<Epimer A<51%.

14. Process according to claim 12, wherein after step g) of crystallization from methanol budesonide is obtained with 44%<Epimer A<51%.

15. Process according to claim 6, wherein the reaction temperature of step b) varies within the range from 0 to +5° C.

16. Process according to claim 7, wherein the reaction time of step b) varies within the range from 120 to 180 minutes.

17. Process according to claim 12, wherein said substep 2) of distilling the methanol is carried out at atmospheric pressure.

* * * * *